United States Patent [19]

Grady et al.

[11] Patent Number: 4,756,016
[45] Date of Patent: Jul. 5, 1988

[54] ASYMMETRIC X-RAY STAND

[75] Inventors: John K. Grady, XRE Corporation, 300 Foster St., Littleton, Mass. 01460; Gordon D. Row, Belmont, Mass.

[73] Assignee: John K. Grady, Harvard, Mass.

[21] Appl. No.: 22,407

[22] Filed: Mar. 6, 1987

[51] Int. Cl.4 .......................... A61B 6/00; H05G 1/02
[52] U.S. Cl. .................................. 378/197; 378/195; 378/193
[58] Field of Search ............... 378/193, 195, 196, 197, 378/198

[56] References Cited
U.S. PATENT DOCUMENTS
3,784,837  1/1974  Holmström .................... 378/197
4,426,725  1/1984  Grady ............................ 378/196

Primary Examiner—Carolyn E. Fields
Assistant Examiner—Joseph A. Hynds
Attorney, Agent, or Firm—James H. Grover

[57] ABSTRACT

An X-ray apparatus is disclosed comprising an angularly adjustable parallelogram formed by two members parallel to a central axis and two members transverse the central axis. A radiation source and a radiation receptor are positioned at one end of the respective parallel members. The apparatus is characterized in that the two transverse members are disposed on opposite sides of the central axis, and one end of both parallel members is offset to the same side of the central axis.

6 Claims, 1 Drawing Sheet

ASYMMETRIC X-RAY STAND

BACKGROUND OF THE INVENTION

U.S. Pat. No. 3,892,967 describes X-ray apparatus wherein the X-ray source and X-ray receptor are mounted at the ends of two horizontal members which with two transverse members form an adjustable parallelogram rotating on the central axis of a support rotor. To maintain the parallelogram stably in balance about the axis the horizontal and transverse members are located in a plane coincident with the central axis and the ends of the horizontal members are offset on opposite sides of the plane. When doctors must approach close to a patient lying on the central axis one or the other of the offset ends obstructs the doctor's access or may even strike the doctor during the rotation of the parallelogram about the central axis.

It is the object of the present invention to improve the doctor's access to at least one side of the patient and minimize the risk of striking him while maintaining the static balance of the parallelogram and the X-ray source and receptor.

SUMMARY OF THE INVENTION

According to the invention X-ray apparatus comprises a main support rotor mounted to turn about a central axis; an angularly adjustable paralellogram formed by two members parallel to the central axis and two members transverse of the central axis; and a radiation source and a radiation receptor respectively at one end of respective parallel members; characterized in that the transverse members are disposed on opposite sides of the central axis, and said one end of both parallel members is offset to the same side of the central axis.

DRAWINGS

Figure 1:
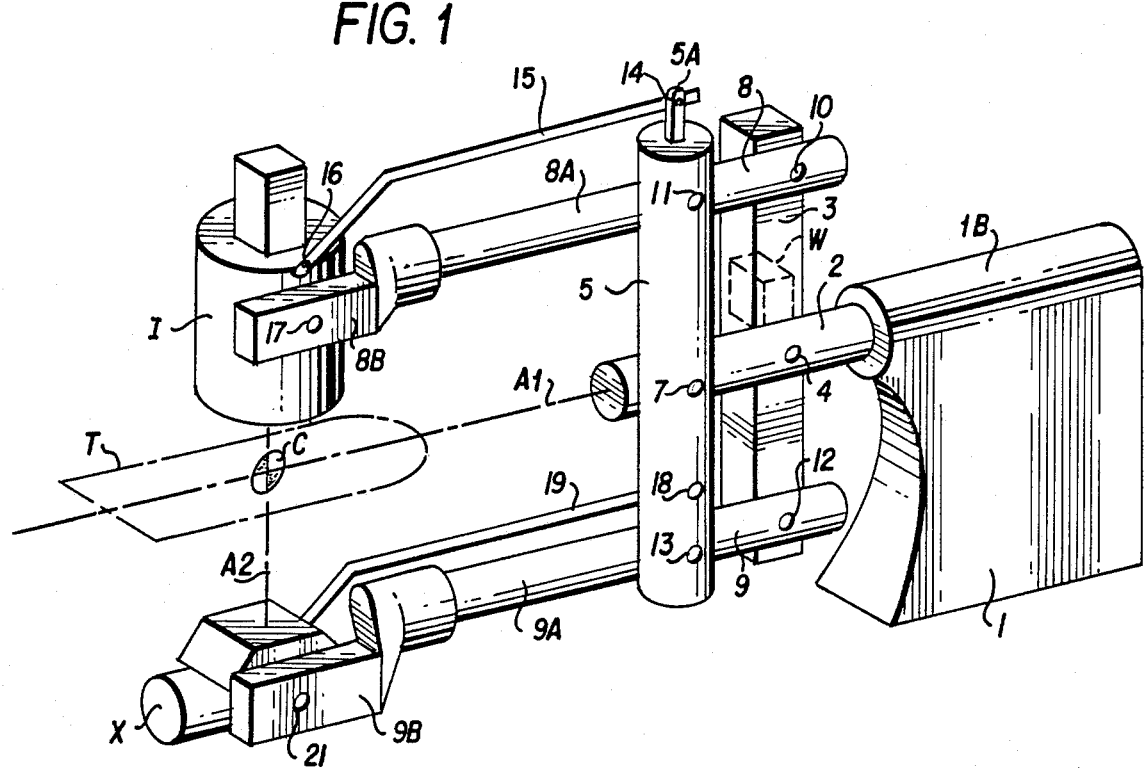
Figure 2:
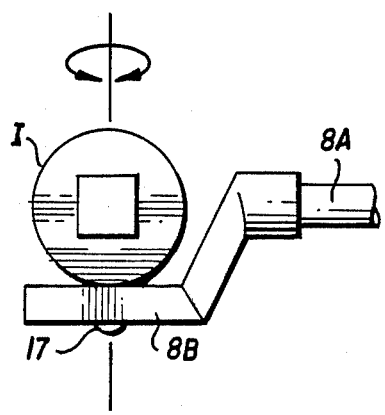
Figure 3:
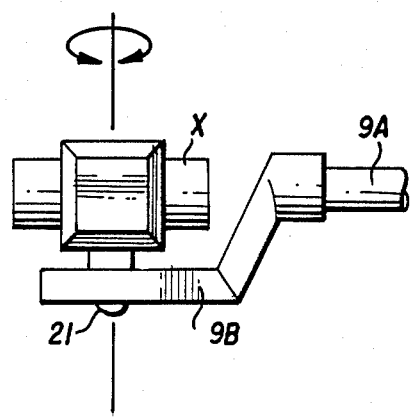

FIG. 1 is an isometric view of a stand supporting an X-ray source and receptor; and FIGS. 2 and 3 are plan views of the source and receptor.

DESCRIPTION

Shown in the figures is an apparatus for X-ray examination of a patient in a fixed position on a radiation-transparent table T. The patient table T is shown in FIG. 1. The patient's heart, for example, would be located at an isocenter C which is at the intersection of the central axis of rotation A1 of the apparatus and of a radiation axis A2 between an X-ray tube X and a radiation image intensifier T. Subjects other than a human organ may be examined, and the radiation receptor 22 may be a ray-sensitive film, fluorescent screen or a scintillation counter. In each case it is desired that the subject be at the isocenter C on the radiation axis A2 which is coincident with the aligned axes of the X-ray tube X and the image receptor I. In neuro and cardiac angiography the human organ is examined radiologically by tilting or angulating the X-ray tube X and image receptor 22 through 360° of angle around the central axis A1 of the system which is around the longitudinal axis of the patient, and also through 90° of angle, for example, in the head to foot direction, that is about a secondary axis perpendicular to the central axis A1 and through the isocenter C. Angulation of the radiation axis A2 about the isocenter is thus possible through a solid angle defined by the 360° angulation about the central axis A1 and the head to foot tilting of the radiation axis.

The apparatus producing such angulation comprises a heavy base 1 anchored to the floor of a hospital or laboratory, the base having a rotary bearing 1B for a central rotor shaft 2 journalled in the bearing. A first transverse member 3 extending generally vertically of the rotor 2 is pivotally attached to the rotor at 4. A second transverse member 5 is pivotally supported at 7 at the left end of the rotor 2. The two transverse members 3 and 5 and two other members, upper and lower arm 8 and 9, are pivotally connected by bearing pins 10, 11, 12 and 13 to form an angularly adjustable parallelogram (3,5,8,9) whose sides are of a fixed length between the pivotal connections (10,11,12,13).

The two other horizontal members 8 and 9 have extensions 8A and 9A outside the parallelogram for distances sufficient to allow the table T and patient P to be located close to the vertical transverse member 5. At the free ends of the extensions 8A and 9A are two pivots 17 and 21 respectively for the image intensifier I and the X-ray tube X. A short extension 5A from the transverse member 5 has a pivot point 14 for a link 15 extending to a pivot point 16 on the image intensifier I. Similarly a second link 19 is connected between a pivot point 18 on the transverse member 5 and a pivot point (not shown) on the X-ray tube X.

According to the invention the transverse members 3 and 5 are disposed on opposite sides of the rotor 2 and its central plane coincident with the radiation axis A2 and the central axis A1, and the end 8B of the upper horizontal member 8 is offset to the same side of the rotor 2 and its central axis A1 as the end 9B of the lower horizontal member 9. The imbalance of the offset of the ends to the same side is countered by a weight W in the transverse member 3 which now is on the other side of the central plane coincident with the central axis. Since the offset of the horizontal member ends is only on one side the other side is left unobstructed above and below the patient table T, and there is no offset to strike a doctor on that other side. As shown in FIG. 1, the links 15 and 19 are similarly offset on opposite sides of the central plane.

We claim:

1. X-ray apparatus for examination of a patient comprising:
   a main support rotor mounted to turn about a central axis lying in a central plane;
   an angularly adjustable parallelogram formed by two members parallel to the central axis and two members transverse of the central axis; and
   a radiation source and a radiation receptor respectively at one end of respective parallel members;
   characterized in that a first transverse member is disposed on one side of said central plane, a second transverse member is disposed on an opposite side of said central plane, offset from said first transverse member, and said one end of both parallel members is offset to the same side of the central plane.

2. Apparatus according to claim 1 wherein the radiation source and receptor define a radiation axis intersecting the central axis at an isocenter.

3. Apparatus according to claim 2 including means rotating the radiation source and receptor maintain them aligned on the radiation axis as the parallelogram is adjusted.

4. Apparatus according to claim 1 including a counter-weight on the parallelogram offset from the central plane oppositely to the offset of the ends of the parallel members.

5. Apparatus according to claim 4 wherein the counter-weight is in a transverse member.

6. Apparatus according to claim 4 including a first link between one end of one transverse member and the radiation receptor and a second link between the opposite end of said one transverse member and the radiation source for holding the source and receptor aligned on the radiation axis, characterized in that the respective links are offset on opposite sides of the central plane.

* * * * *